United States Patent
Nishiuchi et al.

(10) Patent No.: US 11,511,134 B2
(45) Date of Patent: Nov. 29, 2022

(54) PARTICLE THERAPY SYSTEM AND EXTENSION METHOD THEREOF

(71) Applicant: Hitachi, Ltd., Tokyo (JP)

(72) Inventors: Hideaki Nishiuchi, Tokyo (JP); Hiroyuki Satake, Tokyo (JP); Yui Shinozawa, Tokyo (JP); Yujiro Fujisaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 785 days.

(21) Appl. No.: 16/412,591

(22) Filed: May 15, 2019

(65) Prior Publication Data

US 2020/0094077 A1 Mar. 26, 2020

(30) Foreign Application Priority Data

Sep. 21, 2018 (JP) .............................. JP2018-178020

(51) Int. Cl.
| | | |
|---|---|---|
| *A61N 5/10* | (2006.01) | |
| *G21K 1/02* | (2006.01) | |
| *G21K 1/093* | (2006.01) | |
| *G21K 1/00* | (2006.01) | |
| *G21K 5/04* | (2006.01) | |

(52) U.S. Cl.
CPC .............. *A61N 5/1079* (2013.01); *G21K 1/00* (2013.01); *G21K 1/025* (2013.01); *G21K 1/093* (2013.01); *G21K 5/04* (2013.01); *A61N 2005/1087* (2013.01); *A61N 2005/1094* (2013.01)

(58) Field of Classification Search
CPC .... A61N 2005/1087; A61N 2005/1094; A61N 5/1079; G21K 5/04
See application file for complete search history.

(56) References Cited

U.S. PATENT DOCUMENTS

| | | | |
|---|---|---|---|
| 2011/0220809 A1 | 9/2011 | Yajima et al. | |
| 2016/0074676 A1 | 3/2016 | Yajima et al. | |
| 2016/0240350 A1* | 8/2016 | Lane ................... | H01J 37/3007 |
| 2018/0064957 A1 | 3/2018 | Hori et al. | |

FOREIGN PATENT DOCUMENTS

| | | |
|---|---|---|
| CN | 106215333 A | 12/2016 |
| JP | 2018-038628 A | 3/2018 |

OTHER PUBLICATIONS

Toshiba Energy Systems & Solutions Corporation; retrieved on May 13, 2019, <URL:https://www.toshiba-energy.com/en/heavy-ion/product/support.htm>.

\* cited by examiner

*Primary Examiner* — Christine H Matthews
(74) *Attorney, Agent, or Firm* — Mattingly & Malur, PC

(57) ABSTRACT

A particle therapy system includes a building having a first floor and second floors and, a particle beam generator installed on the first floor and configured to generate a particle beam, a first transport system configured to transport a particle beam from the particle beam generator to a first irradiation system in a first treatment room, and a second transport system configured to transport a particle beam to a second irradiation system in a second treatment room, branched from the first transport system, via a second floor. The second transport system has a first bending magnet that bends a particle beam to the direction of the second floor different from the installation surface of the particle beam generator. The building has a shielding wall configured to shield the first floor and the second floor and the second transport system is provided penetrating the shielding wall.

10 Claims, 11 Drawing Sheets

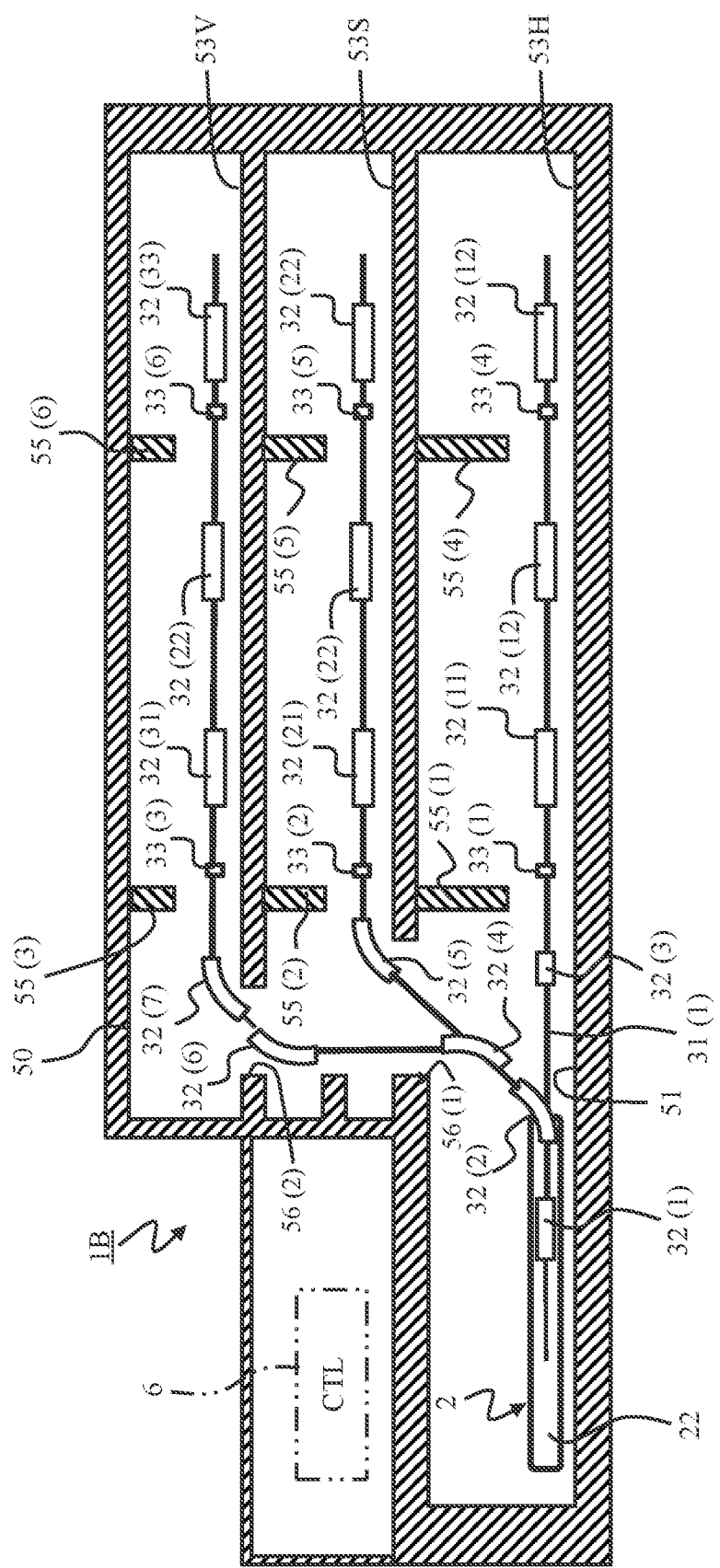

PARTICLE THERAPY SYSTEM AND EXTENSION METHOD THEREOF

CROSS-REFERENCE TO RELATED APPLICATION

The present application claims priority from Japanese application JP 2018-178020, filed on Sep. 21, 2018, the contents of which is hereby incorporated by reference into this application.

TECHNICAL FIELD

The present invention relates to a particle therapy system and an extension method therefor.

BACKGROUND ART

A particle therapy system is known in which a target volume is irradiated with a particle beam of protons or carbon, for example, for treatment (Patent Literature 1).

CITATION LIST

Patent Literature

Patent Literature 1: Japanese Unexamined Patent Application Publication No. 2018-38628

SUMMARY OF INVENTION

Technical Problem

In Patent Literature 1, a system can be updated, such as addition to the system, using time for which no treatment is available, such as nighttime and holidays. However, Patent Literature 1 discloses no method with which a particle therapy system is efficiently extended for a short time in the case in which particle beams are supplied to a floor that is not the installation surface of an accelerator that generates particle beams.

An object of the present invention is to provide a particle therapy system and an extension method therefor that improve extensibility.

Solution to Problem

In order to solve the problem, a particle therapy system according to the present invention is a particle therapy system including: a building having a first floor and a second floor; a particle beam generator installed on the first floor, the particle beam generator being configured to generate a particle beam; a first transport system configured to transport a particle beam from the particle beam generator to a first irradiation system in a first treatment room; and a second transport system configured to transport a particle beam branched from the first transport system, via the second floor, to a second irradiation system in a second treatment room. The second transport system has a first bending magnet configured to bend a particle beam to a direction of the second floor different from an installation surface of the particle beam generator. The building has a shielding wall shielding the first floor and the second floor. The second transport system is provided penetrating the shielding wall on a rear side of the first bending magnet in a traveling direction of a particle beam.

Advantageous Effects of Invention

According to the present invention, the second transport system configured to transport a particle beam to the second irradiation system in the second treatment room can be provided penetrating the shielding wall on the rear side of the first bending magnet configured to bend a particle beam in the direction of the second floor different from the installation surface of the particle beam generator. Thus, the system can be extended to the second treatment room side with no influence of the particle beam generator.

BRIEF DESCRIPTION OF DRAWINGS

FIG. 11 is a cross sectional view taken along the direction of arrow X-X in FIG. 10.

DESCRIPTION OF EMBODIMENTS

In the following, embodiments of the present invention will be described with reference to the drawings. A particle therapy system according to an embodiment includes a configuration taking into account of extensibility beforehand, as described later. In the following, a particle beam is sometimes referred to as a "beam".

Figure 1:
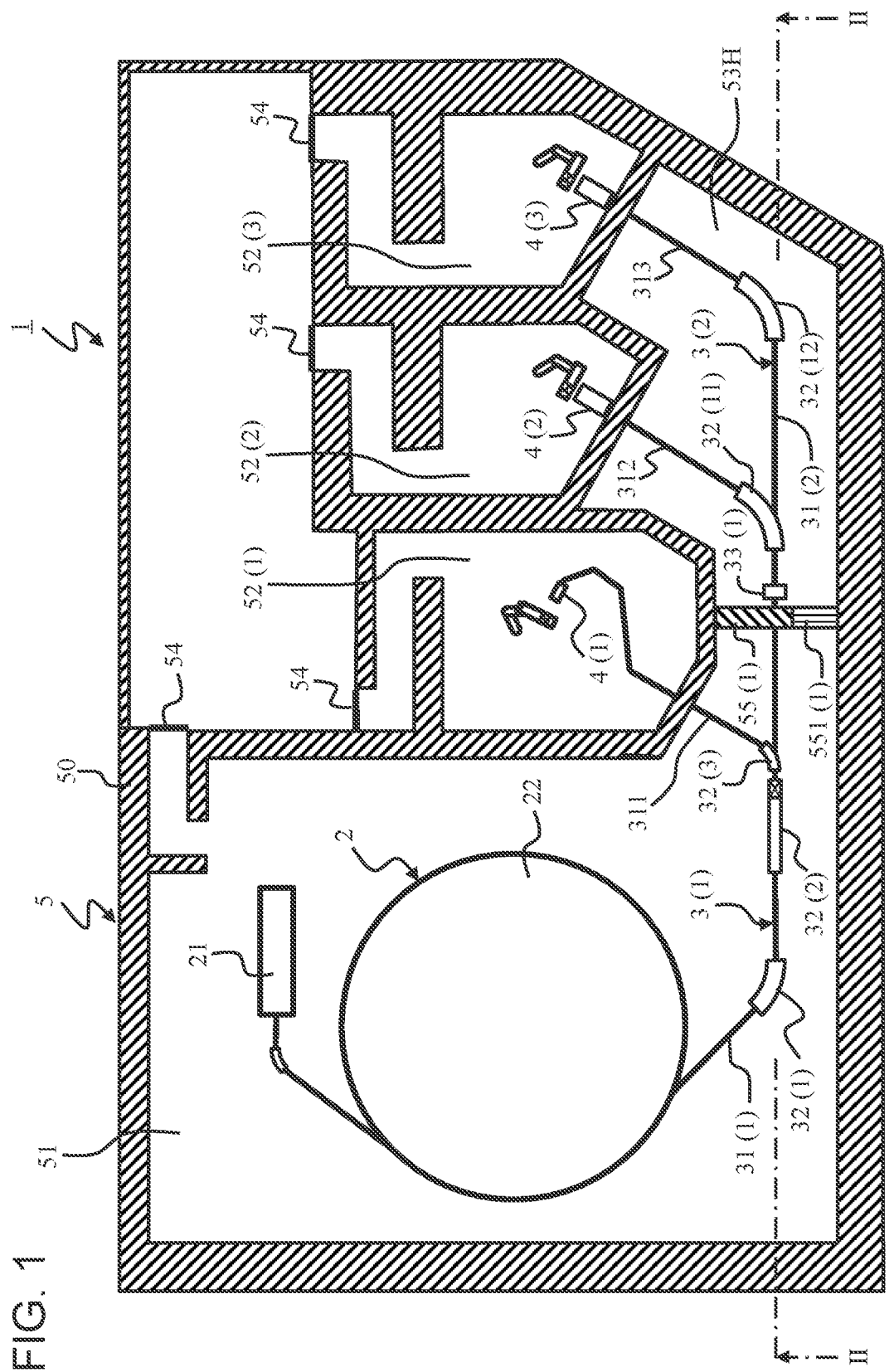
FIG. 1 is a plan view of a particle therapy system.
Figure 8:
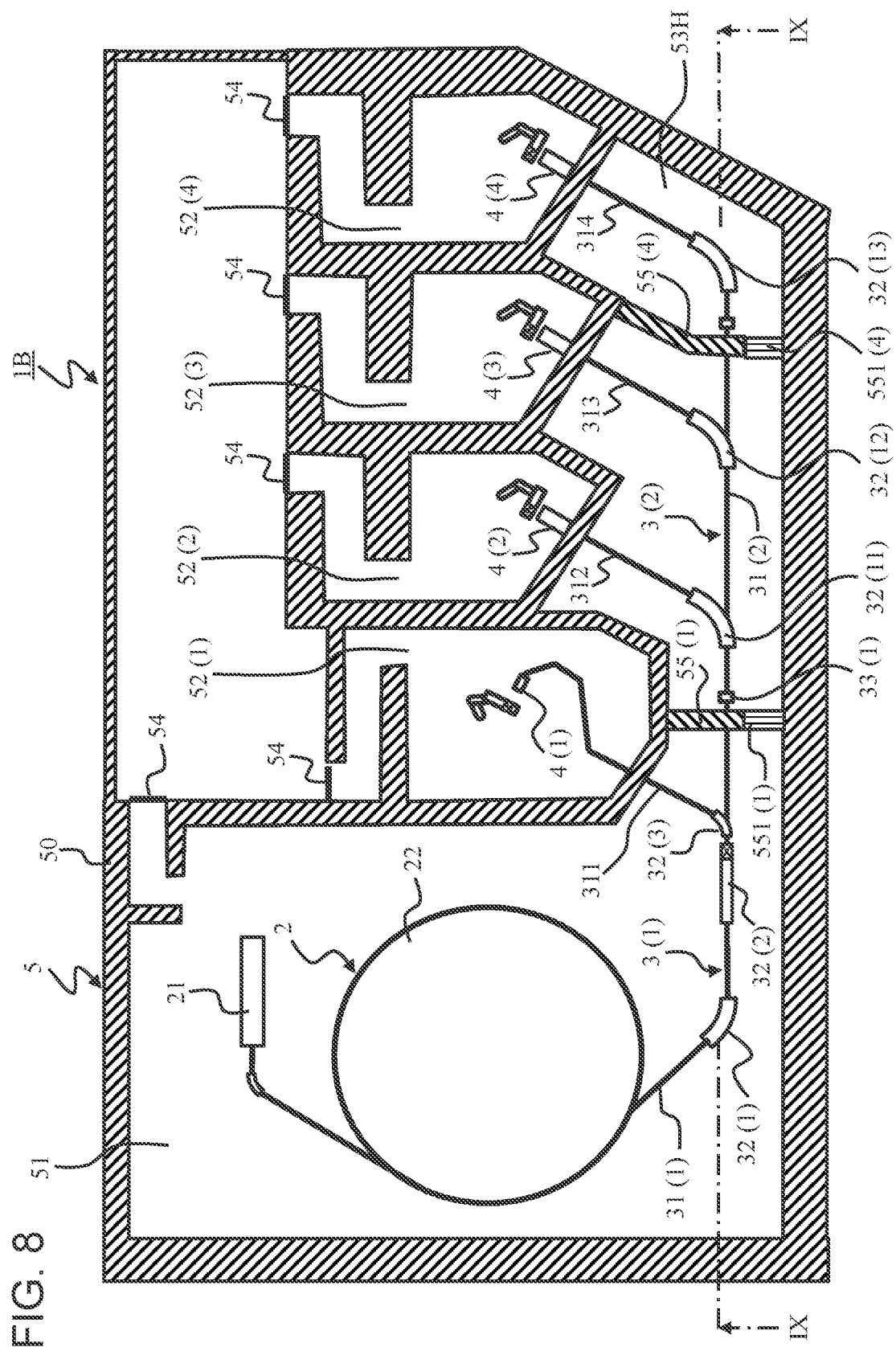
FIG. 8 is a plan view of a particle therapy system according to a third embodiment.

In the embodiment, in a building 5 constituting a particle therapy system 1, there are prepared a treatment room 52(1) that operates in the beginning of installation of the particle therapy system 1 as well as treatment rooms 52(2) to 52(4) for extension taking into account of an increase in the number of treatment rooms in future. The treatment rooms 52(2) and 52(3) are shown in FIG. 1, and the treatment room 52(4) is shown in FIG. 8.

In the embodiment, in a beam transport chamber 53, a shielding wall 55 is provided between a first beam transport line 3(1) that transports a beam to the treatment room 52(1) that operates in the beginning of installation and a second beam transport line 3(2) that transports a beam to the treatment rooms 52(2) to 52(4) for extension. The first beam transport line 3(1) is an example of "a first transport system". The second beam transport line 3(2) is an example of "a second beam transport system".

In the embodiment, a first bending magnet 32(2) is provided at the branch point between the treatment room 52(1) that operates in the beginning of installation and the second beam transport line 3(2) that transports a beam to the treatment rooms 52(2) to 52(4) in future. The second beam transport line 3(2) that transports a beam to the treatment rooms 52(2) to 52(4) in future is installed beforehand over the shielding wall 55 of the beam transport chamber 51, and the end of the second beam transport line 3(2) is closed by a breaking unit 33, such as a gate valve, until the treatment rooms 52(2) to 52(4) in future are installed.

In the particle therapy system according to the embodiment, the second beam transport line 3(2) that transports a beam to the treatment rooms 52(2) to 52(4) in future has a section that is installed in advance, the section from the start to bending the beam toward second floors 53V and 53S having a horizontal surface that is different from the horizontal surface on which an accelerator 22 is installed.

As described above, in the embodiment, the breaking unit 33, such as a gate valve, is provided on the second beam transport line 3(2). Specifically, in the second beam transport line 3(2), the end of the portion that is installed prior to extending the treatment rooms is hermetically closed by providing the breaking unit 33, such as a gate valve. Thus, the leakage dose is reduced while the vacuum degree on the upstream side (the upstream side in the moving direction of the particle beam) of the breaking unit 33, such as a gate valve, is maintained, and hence a system can be additionally provided for a short time on the downstream side of the breaking unit 33, such as a gate valve.

In the embodiment, on the bending magnet 32(2) provided at the branch point between beam transport to the first treatment room 52(1) and beam transport to the second treatment rooms 52(2) to 52(4), an interlock may be provided in order not to transport a beam to the treatment rooms 52(2) to 52(4) in future until the additional construction of the treatment rooms 52(2) to 52(4) in future is completed.

According to the embodiment thus configured, treatment rooms can be additionally provided for a short time corresponding to an increase in the number of treatment patients, for example, while the initial installation cost of the particle therapy system 1 is reduced. According to the embodiment, the treatment rooms 52(2) to 52(4) can be additionally provided without stopping treatment at the treatment room 52(1) that already operates. Thus, in the embodiment, the continuation of treatment and the ensuring the treatment income of without stopping the particle therapy system 1 for a long time.

First Embodiment

Figure 2:
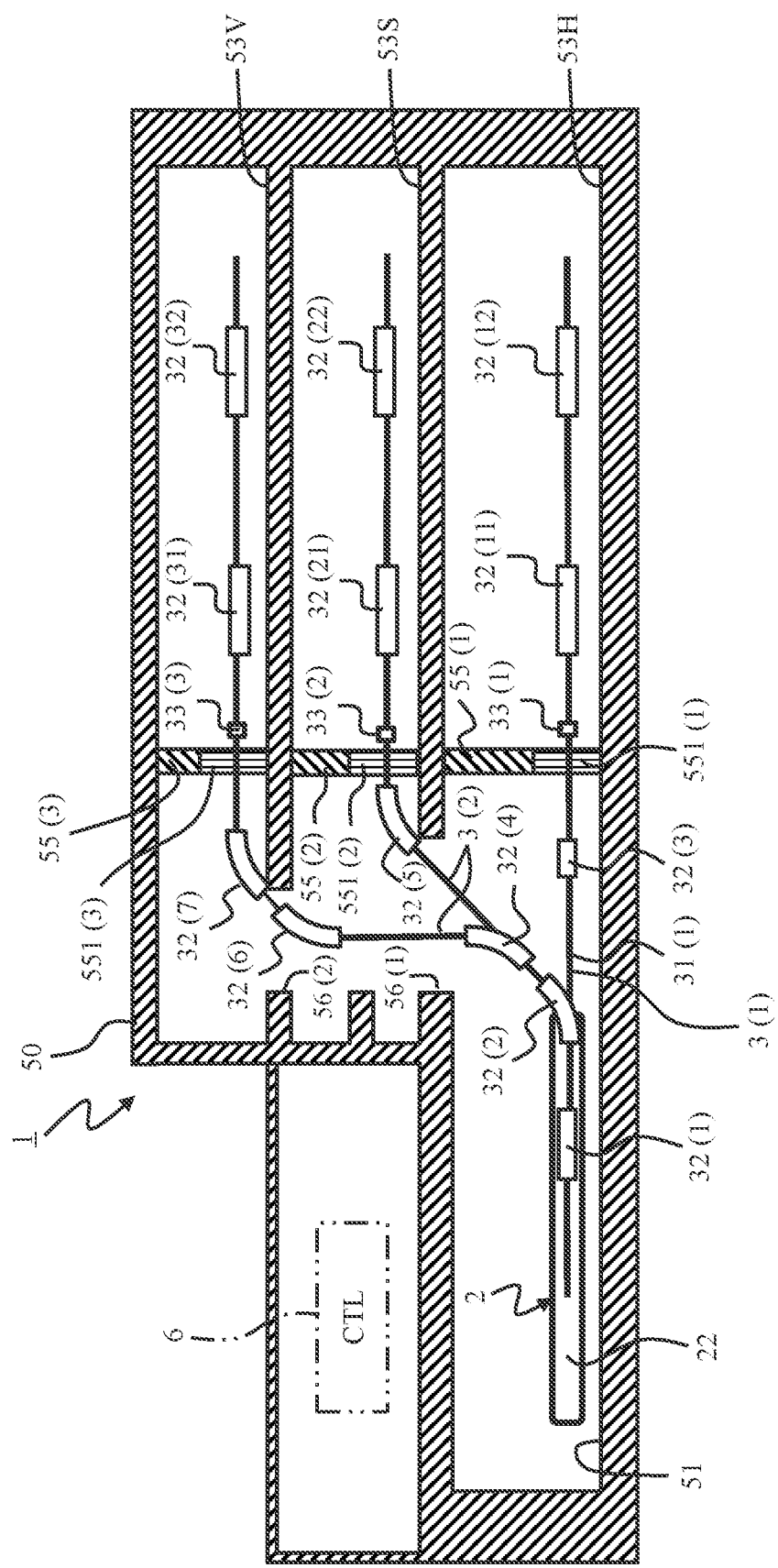
FIG. 2 is a cross sectional view taken along the direction of arrow II-II in FIG. 1.

Referring to FIGS. 1 to 5, a first embodiment will be described. FIG. 1 is a plan view of a particle therapy system 1. FIG. 2 is a cross sectional view taken along the direction of arrow II-II in FIG. 1.

The particle therapy system 1 is provided at a building 5, a tertiary care ward of a hospital, for example. The building 5 is constructed with a strong wall 50 so as to include an accelerator chamber 51, treatment rooms 52(1) to 52(3), and a beam transport chamber 53, for example. At the chambers 51 to 53, an entrance 54 is appropriately provided (the entrance to the beam transport chamber 53 is not shown). The accelerator chamber 51 is an example of "a first floor". In the beam transport chamber 53 having a three-layer structure, the second layer and the third layer are examples of "a second floor".

The treatment room 52(1) is an example of "a first treatment room". The treatment room 52(1) is a proton treatment room where a target volume is irradiated with a proton beam that is "a first particle beam". The treatment rooms 52(2) and 52(3) are examples of "a second treatment room". The second treatment rooms 52(2) and 52(3) are carbon treatment rooms where a target volume is irradiated with a carbon beam that is "a second particle beam".

As shown in FIG. 2, the beam transport chamber 53 according to the embodiment has a three-layer structure. A first layer 53H is a horizontal direction floor where a beam is applied to the inside of the second treatment rooms 52(2) and 52(3) from the horizontal direction. A second layer 53S is a skew direction floor where a beam is applied to the inside of the second treatment rooms 52(2) and 52(3) from a skew direction. A third layer 53V is a vertical direction floor where a beam is applied to the inside of the second treatment rooms 52(2) and 52(3) from the vertical direction. In the case in which the layers are not distinguished, the chambers are referred to as the beam transport chamber 53. The skew direction floor 53S and the vertical direction floor 53H correspond to "a second floor".

At the beam transport chambers 53H, 53S, and 53V, a shielding wall 55 is erected, located on the boundary to the accelerator chamber 51. On the beam transport chamber 53H, a shielding wall 55(1) is vertically provided from its floor to its ceiling. Similarly, also on the beam transport chamber 53S, a shielding wall 55(2) is vertically provided from its floor to its ceiling. Also on the beam transport chamber 53V, a shielding wall 55(3) is vertically provided from its floor to its ceiling.

The shielding walls 55(1) to 55(3) are provided in the midway point of the beam transport passage, as located on the rear side of a bending magnet 32(2) such that the accelerator chamber 51 where a particle beam generator 2 is installed is isolated from the beam transport chamber 53. The shielding walls 55(1) to 55(3) may include removable regions 551(1) to 551(3). In the extension of the system (the addition of the system) to the treatment rooms 52(2) and 52(3), an entrance for workers can be formed by removing the regions 551(1) to 551(3). Note that the shielding walls 55(1) to 55(3) may be entirely demolished and removed as well as the regions 551(1) to 551(3). In this case, a wider work passage can be obtained.

In addition to the building 5, the particle therapy system 1 includes the particle beam generator 2, beam transport lines 3(1) and 3(2), irradiation systems 4(1) to 4(3), a control system 6(see FIG. 2), and a power supply device, not shown, for example.

The particle beam generator 2 according to the embodiment is a hybrid device that can generate a plurality of charged particle beams, such as a proton beam or carbon beam, by switching. In the following, the charged particle beam is sometimes abbreviated as a "beam".

The particle beam generator 2 is installed on the accelerator chamber 51. The particle beam generator 2 includes an ion source (not shown), a preaccelerator 21, and a circular accelerator 22, for example. The circular accelerator 22 may be a synchrotron or a cyclotron, for example.

To the upstream side of the preaccelerator 21, the ion source, not shown, is connected, and to the downstream side of the preaccelerator 21, the circular accelerator 22 is connected. Here, in the embodiment, "the upstream side" or "the downstream side" is based on the traveling direction of the beam. The direction in which the beam comes in is "the upstream side" or "the front side", and the direction in which the beam goes out is "the downstream side" or "the rear side".

The beam transport line 3(1) is an example of "a first beam transport system". The beam transport line 3(1) is provided on the beam transport chamber 53. The beam transport line 3(1) is connected to the downstream side of the particle beam generator 2, and connects the particle beam generator 2 to the irradiation system 4(1) in the proton treatment room 52(1).

A proton beam generated at the particle beam generator 2 is delivered to the irradiation system 4(1) installed in the treatment room 52(1) through the beam transport line 3(1). The irradiation system 4(1) irradiates a target volume 7 of a patient (see FIG. 3) with the proton beam. The irradiation system 4(1) is an example of "s first irradiation system".

The beam transport line 3(1) includes the beam transport passage 31(1) and a plurality of bending magnets 32(1), 32(2), and 32(3) provided on the beam transport passage 31(1), for example. On the beam transport passage 31(1), a quadrupole magnet, a steering magnet, and a profile monitor (these components are not shown) are provided, for example, in addition to the bending magnet 32(1).

The bending magnet 32(1) is provided in the midway point of the beam transport passage 31(1), and controls the direction of a beam passing the beam transport passage 31(1) corresponding to a control signal from the control system 6. The bending magnet 32(2) corresponds to "a first bending magnet", and bends a beam in the directions of the second floors 53S and 53V that are different from the installation surface of the particle beam generator 2 installed on the accelerator chamber 51.

That is, as shown in FIG. 2, the bending magnet 32(2) controls the beam orientation such that beams are individually transported toward the floors 53S and 53V having the surface parallel with the floor surface of the accelerator chamber 51.

On the horizontal surface the same as the accelerator chamber 51, the bending magnet 32(3) supplies a beam to any one of the irradiation system 4(1) in the treatment room 52(1) or the irradiation systems 4(2) and 4(3) in the treatment rooms 52(2) and 52(3). On the rear side of the shielding wall 55(1), a breaking unit 33(1), such as a gate valve, that holds a vacuum degree is provided on The beam transport line 31(1).

The beam bent in the height direction of the floor surface of the accelerator chamber 51 (the installation surface of the particle beam generator 2 or the horizontal surface of the accelerator 22) by the bending magnet 32(2) is supplied to the skew direction floor 53S or the vertical direction floor 53V by a bending magnet 32(4).

On the skew direction floor 53S, the is delivered in the directions of the treatment rooms 52(2) and 52(3) by a bending magnet 32(5) through a breaking unit 33(2), such as a gate valve. The beam reaches the skew direction floor 53S through the beam transport passage penetrating the shielding wall 55(2), and is supplied to the treatment room 52(2) by the bending magnet 32(21) or to the treatment room 52(3) by the bending magnet 32(22).

Similarly, to the vertical direction floor 53V, the beam is delivered through the bending magnets 32(4) and 32(5) and bending magnets 32(6) and 32(7). The beam reaches the vertical direction floor 53V through the beam transport passage penetrating the shielding wall 55(3) and the breaking unit 33(3), such as a gate valve, and is supplied to the treatment room 52(2) by a bending magnet 32(31) or to the treatment room 52(3) by a bending magnet 32(3).

Figure 3:
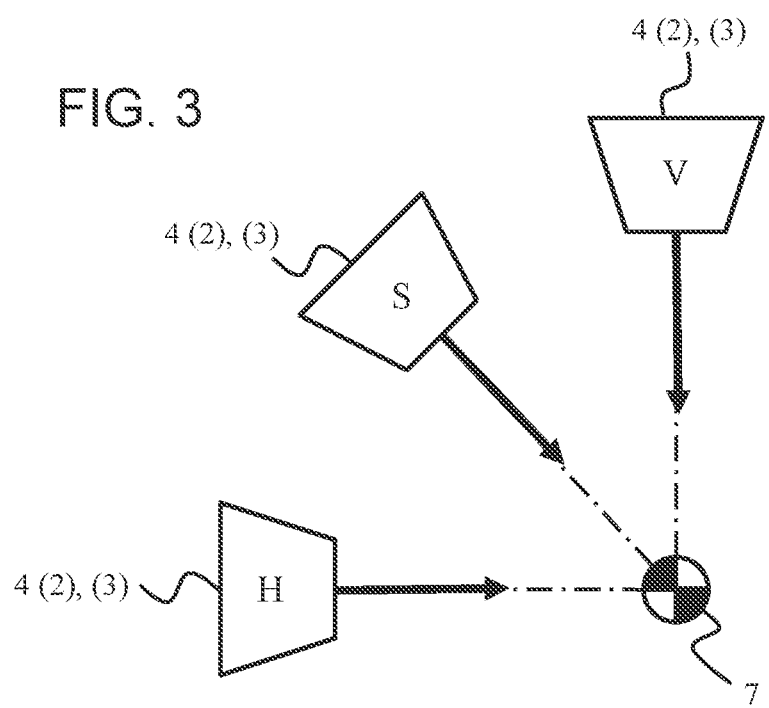
FIG. 3 is an illustration of irradiating a target volume with particle beams from a horizontal direction (H), a vertical direction (V) and a skew direction (S) in the inside of a second treatment room.

As shown in FIG. 3, the irradiation systems 4(2) and 4(3) provided on the carbon treatment rooms 52(2) and 52(3) irradiate the target volume 7 with a carbon beam supplied from the hybrid particle beam generator 2 from the horizontal direction H, the skew direction S, or the vertical direction V.

That is, in the case in which a carbon beam is used as a beam, the beam has to be applied to the target volume 7 from the horizontal direction as well as from the skew direction or the vertical direction.

In the embodiment, the hybrid particle beam generator 2 that can output a beam by switching between a proton beam and a carbon beam is installed on the building 5. In the embodiment, the proton treatment room 52(1) having the irradiation system 4(1), such as a rotating gantry, and the carbon treatment rooms 52(2) and 52(3) where a beam is applied from the horizontal direction, the skew direction, or the vertical direction are provided in the inside of the building 5. Thus, in the embodiment, treatment can be performed using a particle beam suitable for a target volume that is a treatment target in one facility.

Figure 4:
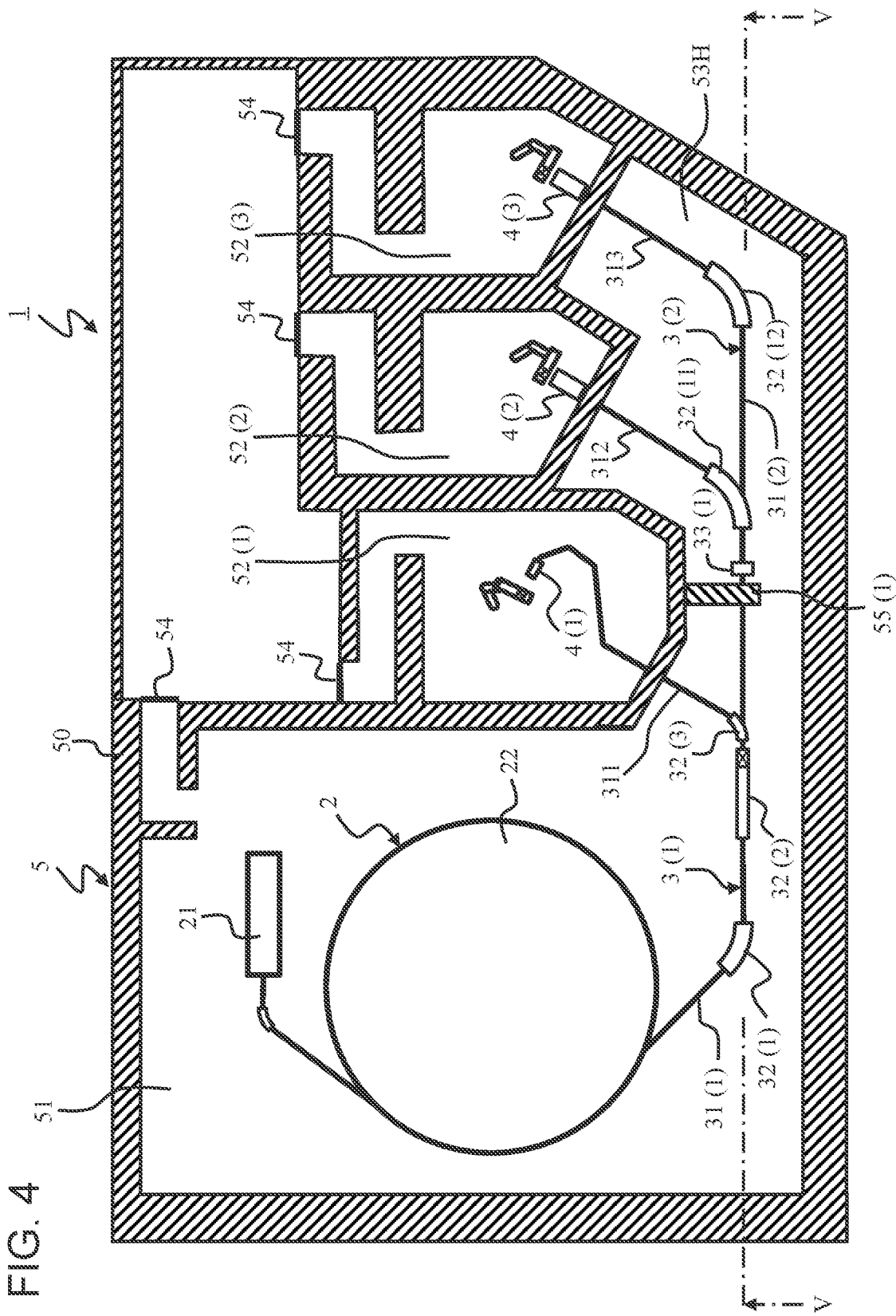
FIG. 4 is a plan view of the particle therapy system with a shielding wall partially removed.
Figure 5:
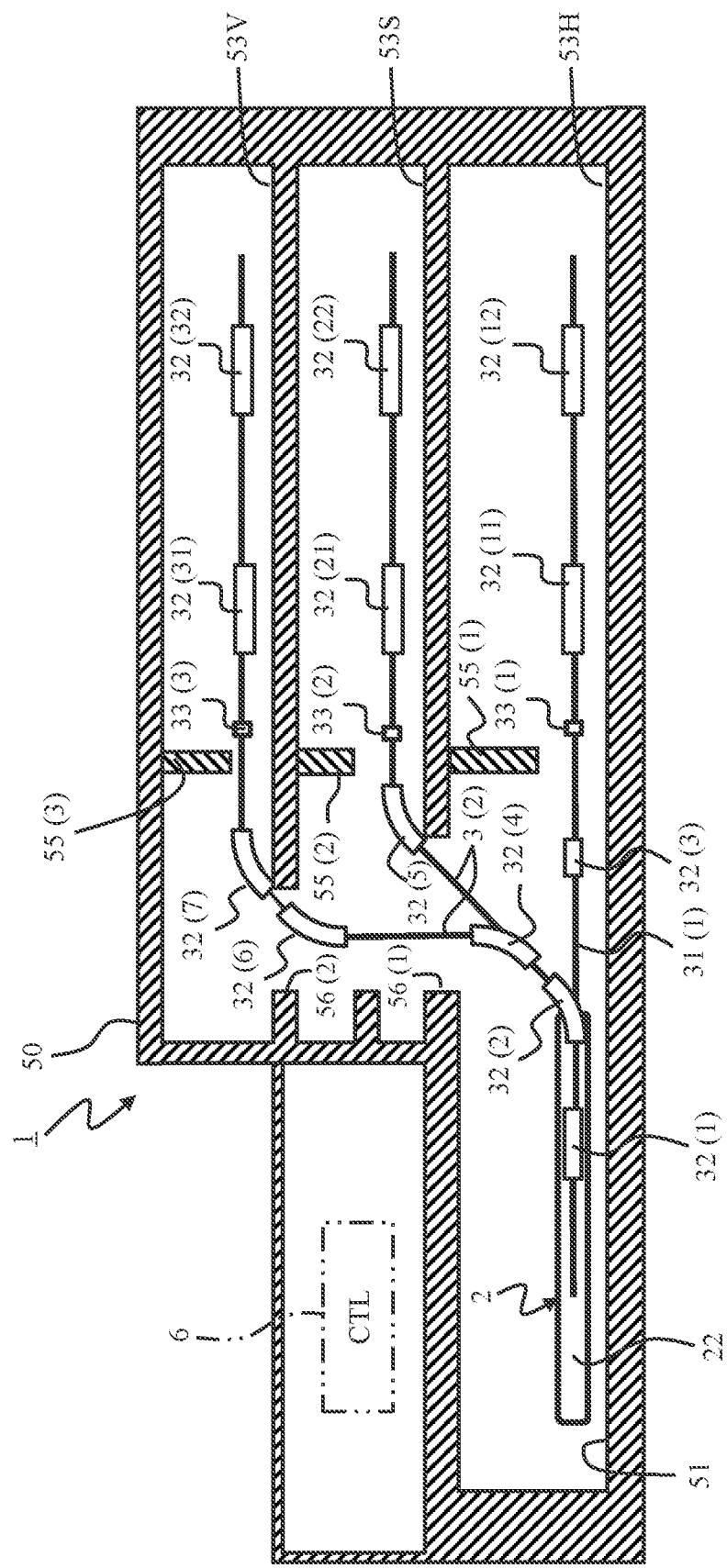
FIG. 5 is a cross sectional view taken along the direction of arrow V-V in FIG. 4.

FIGS. 4 and 5 are diagrams of the state in which the shielding wall 55 is partially removed. In he addition of the treatment rooms 52(2) and 52(3), the regions 551(1) to 551(3) that are a part of the shielding walls 55(1) to 55(3) are removed. Thus, a work passage coupling the accelerator chamber 51 to the beam transport chamber 53 is formed in the inside of the building 5.

Procedures in the extension of the particle therapy system 1 will be described.

(S1) The building 5 having the accelerator chamber 51, the treatment rooms 52(1) to 52(3), and the beam transport chamber 53 is constructed, the particle beam generator 2 is installed on the accelerator chamber 51, and the irradiation system 4(1) is installed on the proton treatment room 52(1). Before construction of extension, treatment using a proton beam can be performed in the proton treatment room 52(1). Before construction of extension, the ends of the beam transport passages passing the shielding walls 55(1) to 55(3) are closed by the breaking units 33(1) to 33(3), such as a gate valve.

(S2) After the extension of treatment rooms is determined (a predetermined timing is reached), the irradiation systems 4(2) and 4(3) are installed on the carbon treatment rooms 52(2) and 52(3). The irradiation systems 4(2) and 4(3) are connected to the particle beam generator 2 through the breaking units 33(1) to 33(3), such as a gate valve, and the group of the bending magnets 32. The bending magnets 32(11), 32(12), 32(21), 32(22), 32(31), and 32(32) necessary for the extension of the system are additionally installed after extension is determined. The group of the bending magnets 32 additionally installed is connected to the control system 6 and to the power supply device (not shown).

(S3) The added portions of the system are vacuumed, and the parts (1) to 551(3) of the shielding walls 55(1) to 55(3) are removed. The shielding walls 55(1) to 55(3) may be entirely removed.

According to the embodiment thus configured, the second transport system 3(2) has the first bending magnet 32(2) that bends a particle beam to the direction of the second floors 53S and 53V that are different from the installation surface of the particle beam generator 2. On the building 5, the shielding wall 55 that shields the first floor 51 and the second floors 53S and 53V is provided. The second transport system 3(2) is provided penetrating the shielding wall 55 on the rear side of the first bending magnet 32(2) in the traveling direction of the particle beam.

Thus, according to the embodiment, the particle beam generated at the particle beam generator 2 can be delivered to the directions of the floors 53S and 53V that are different from the installation surface of the particle beam generator 2, and hence the particle beam can be adapted to the irradiation systems 4(2) and 4(3) having the irradiation angle almost fixed.

According to the embodiment, the shielding wall 55 is provided such that the first floor 51 (the accelerator chamber 51) is separated from the second floors 53S and 53V. Thus, treatment in the treatment room 52(1) is started in advance, and treatment in the other treatment rooms 52(2) and 52(3) can be added later. Accordingly, extensibility can be obtained while the initial installation cost of the particle therapy system 1 is reduced.

According to the embodiment, the breaking units 33(1) to 33(3), such as a gate valve, are provided located on the rear side of the shielding walls 55(1) to 55(3), in the midway point of the beam transport passage through which the beam is supplied to the treatment room 52(1) that is the existing facility and the treatment rooms 52(2) and 52(3) that are the extended facilities. Thus, extension work can be performed for a short time while treatment in the treatment room 52(1) that is the existing facility is continued.

The gate valve (not shown) is provided on the rear side of the bending magnets 32(11), 32(21), and 32(31) for the treatment room 52(2) as well as the gate valve (not shown) is provided on the rear side of the bending magnets 32(12), 32(22), and 32(32) for the treatment room 52(3), and hence the treatment rooms 52(2) and 52(3) can be isolated from the system. Thus, the updates and maintenance of the irradiation system 4 can also be performed without stopping treatment in the other treatment rooms.

Second Embodiment

Figure 6:
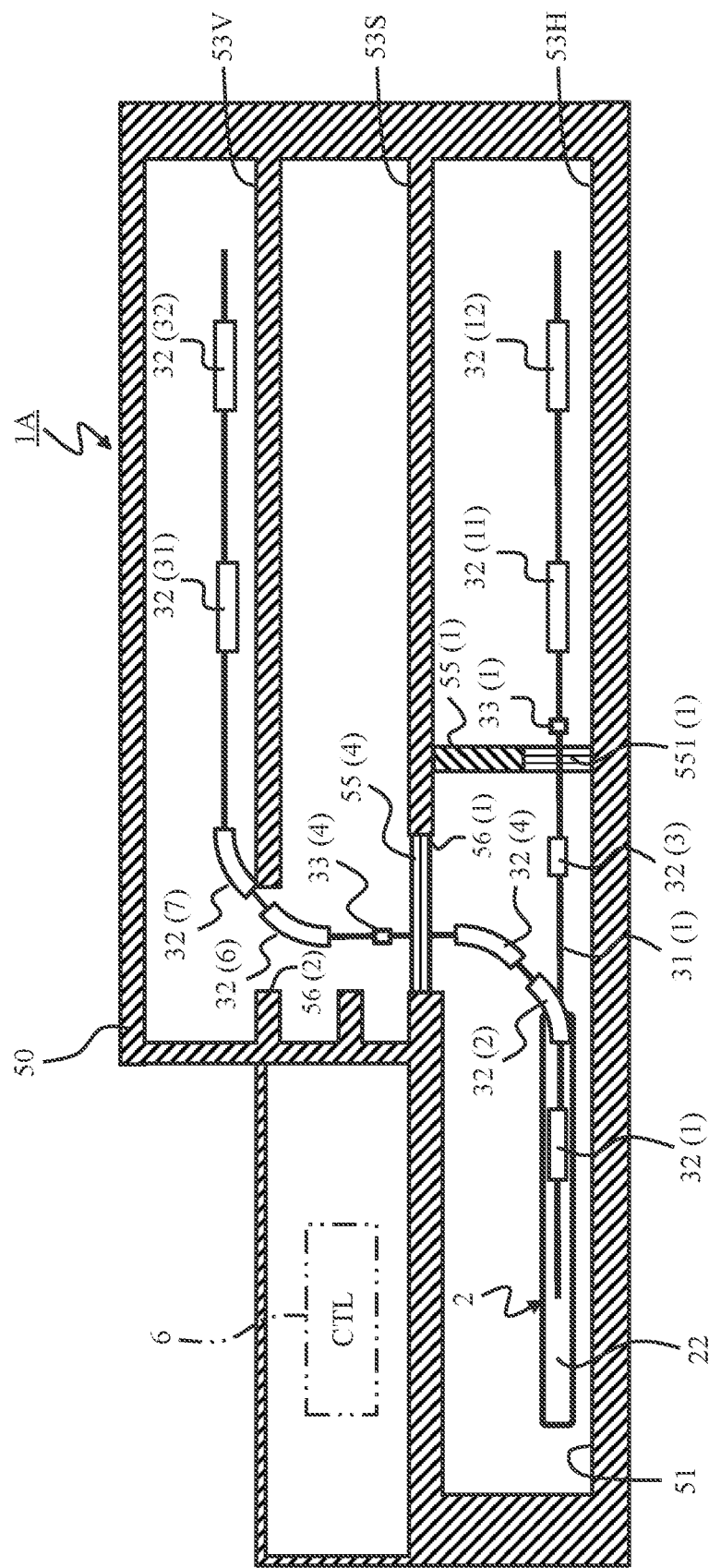
FIG. 6 is a cross sectional view of a particle therapy system according to a second embodiment.
Figure 7:
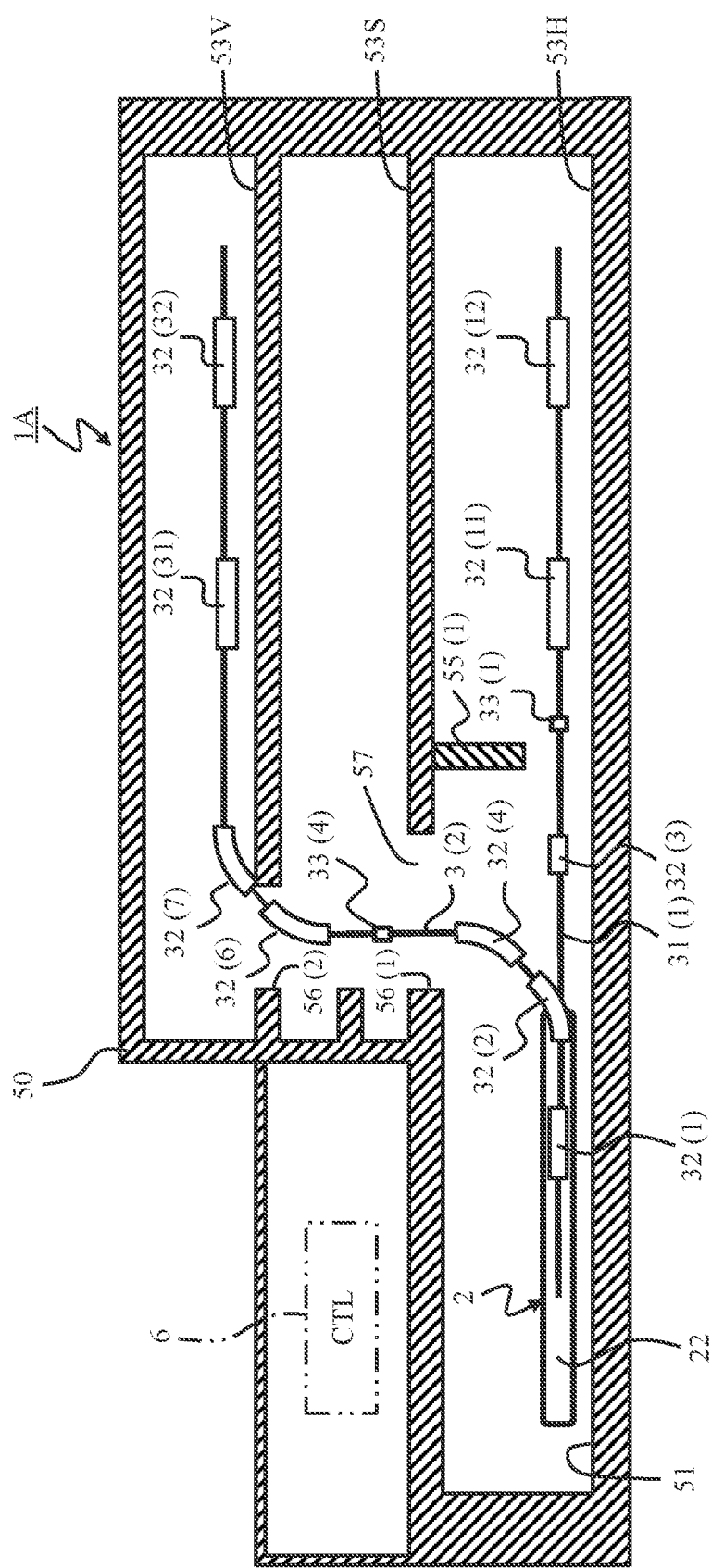
FIG. 7 is a cross sectional view of the particle therapy system with a shielding wall partially removed.

Referring to FIGS. 6 and 7, a second embodiment will be described. The following embodiments including the embodiment correspond to the exemplary modifications of the first embodiment, and the differences from the first embodiment will be mainly described. In the embodiment, a shielding wall 55(4) is provided in parallel with second floors 53S and 53V such that a first floor 51 is separated from second floors 53S and 53V.

FIG. 6 is a plan view of a particle therapy system 1A according to the embodiment. FIG. 7 shows the state in which the shielding wall 55(4) and a shielding wall 55(1) are partially removed.

In the first embodiment, the shielding walls 55(2) and 55(3) are erected from the floor surfaces to the ceilings of the skew direction floor 53S and the vertical direction floor 53V that are second floors. Instead, in the embodiment, the shielding wall 55(4) is provided in parallel with a floor surface 56(1) of the skew direction floor 53S such that the first floor 51 is separated from the second floors 53S and 53V.

That is, the second floors 53S and 53V according to the embodiment are provided on the parallel floor surface 56(1) at a height different from the height of the first floor 51 (the installation surface of a particle beam generator 2), and the first floor 51 communicates with the second floors 53S and 53V through an opening 57 (see FIG. 7). Therefore, in the embodiment, the shielding wall 55(4) is provided on the floor surface 56(1) of the skew direction floor 53S such that the opening 57 is covered.

In the extension of the system, a work passage is formed by removing the shielding wall 55(4) and a part 551(1) of the shielding wall 55(1).

The embodiment thus configured also exerts the operation and effect similar to the first embodiment. In the embodiment, the shielding wall 55(4) is provided so as to cover the opening 57 that communicates the first floor 51 with the second floors 53S and 53V, and hence the installation costs of the shielding wall can be reduced more than in the first embodiment.

Third Embodiment

Figure 9:
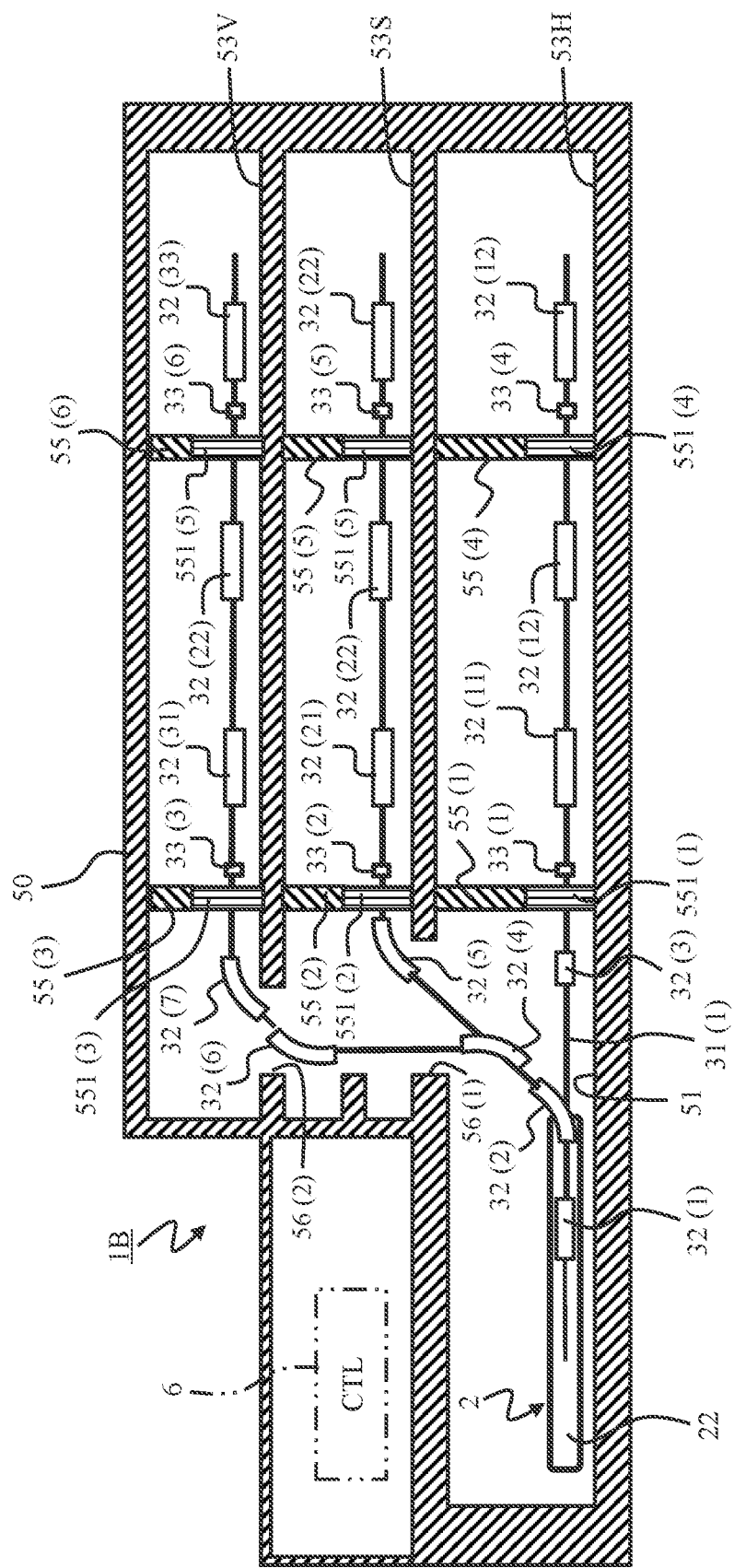
FIG. 9 is a cross sectional view taken along the direction of arrow IX-IX in FIG. 8.
Figure 10:
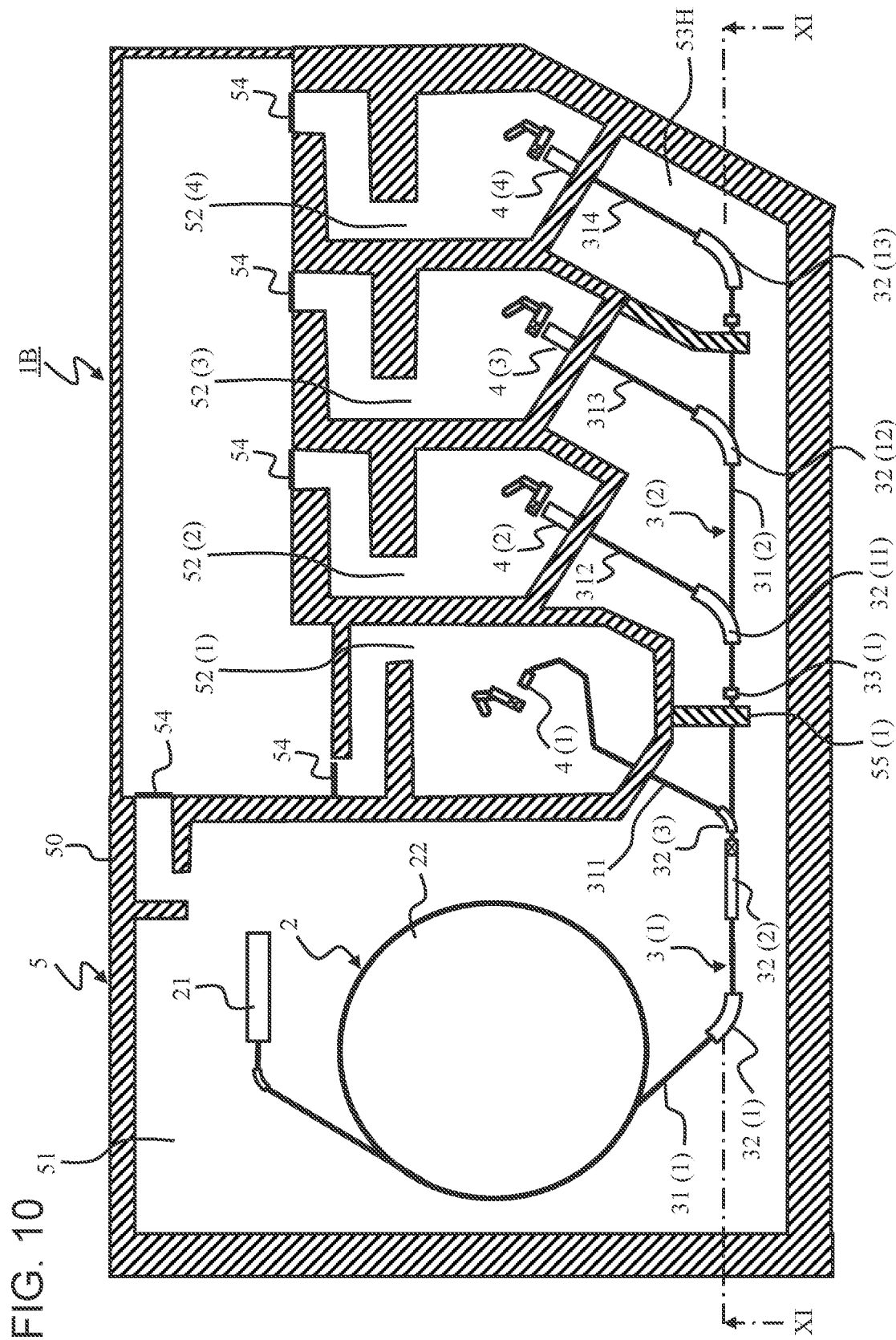
FIG. 10 is a plan view of the particle therapy system with a shielding wall partially removed.

Referring to FIGS. 8 to 11, a third embodiment will be described. In the embodiment, the extension portions of the system are grouped. FIG. 8 is a plan view of a particle therapy system 1B. FIG. 9 is a cross sectional view taken along the direction of arrow IX-IX in FIG. 8. FIGS. 10 and 11 show the state in which a shielding wall 55 is partially removed.

The particle therapy system 1B according to the embodiment includes one proton treatment room 52(1) and three carbon treatment rooms 52(2) to 52(4). The treatment rooms 52(2) to 52(4) that are extension targets include two groups. One group is configured of two carbon treatment rooms 52(2) and 52(3). The other group is configured of one carbon treatment room 52(4). The one group and the other group are shielded with a shielding wall 55(4).

To the treatment rooms 52(2), 52(3), and 52(4), a beam is supplied from a particle beam generator 2 through breaking units 33(1) to 33(3), such as a gate valve, and bending magnets 32(11) to 32(13), 32(21) to 32(23), 32(31) to 32(33), and any other components.

The embodiment thus configured also exerts the operation and effect similar to the first embodiment. In the particle therapy system 1B according to in the embodiment, one or a plurality of treatment rooms 52 is grouped, and the system can be extended step by step. Thus, the system can be efficiently extended corresponding to the number of patients, for example, and this enables the improvement of convenience.

Note that the present invention is non-limiting to the foregoing embodiments. A person skilled in the art can variously add and modify, for example, within the scope of the present invention. The foregoing the embodiments are non-limiting to exemplary configurations shown in the accompanying drawings. The configurations and processing methods of the embodiments can be appropriately modified within the scope of achieving an object of the present invention. For example, the shielding wall may be provided on the near side of the first bending magnet (the accelerator side).

The components the present invention can be optionally selected. The invention including the selected configuration is also included in the present invention. The configuration described in claims can be combined other than the combination explicit in claims.

LIST OF REFERENCE SIGNS

1, 1A, 1B: Particle therapy system
2: Beam generator
3: Beam transport system
4: Irradiation system
5: Building
6: Control system
21: Preaccelerator
22: circular accelerator
31: Beam transport passage
32: Bending magnet
33: Gate valve
51: Accelerator chamber
52: Treatment room 53: Beam transport chamber
55: Shielding wall

The invention claimed is:

1. A particle therapy system comprising:
a building having a first floor and a second floor;
a particle beam generator installed on the first floor, the particle beam generator being configured to generate a particle beam;
a first transport system configured to transport a particle beam from the particle beam generator to a first irradiation system in a first treatment room; and
a second transport system configured to transport a particle beam branched from the first transport system, via the second floor, to a second irradiation system in a second treatment room,
wherein the second transport system has a first bending magnet configured to bend a particle beam to a direction of the second floor, the second floor having a surface that is at a different height from an installation surface of the particle beam generator,
wherein the building has a shielding wall shielding the first floor and the second floor,
wherein the second transport system penetrates the shielding wall on a rear side of the first bending magnet in a traveling direction of a particle beam,
wherein a gate valve is provided on a rear side of the shielding wall on the traveling direction of the particle beam in a midway point of the second transport system,
wherein the second transport system is blocked by the gate valve,
wherein the second transport system is connected, at a predetermined timing, to the second irradiation system in the second treatment room,
wherein the gate valve is opened after an inside of the second transport system is maintained at a vacuum, and
wherein at least a portion of the shielding wall is removed at a predetermined time of expanding the first treatment room by adding the second treatment room.

2. The particle therapy system according to claim 1, wherein the shielding wall is erected on the second floor so as to separate the first floor from the second floor.

3. The particle therapy system according to claim 1, wherein the shielding wall is provided in parallel with the second floor so as to separate the first floor from the second floor.

4. The particle therapy system according to claim 1, wherein the first transport system is connected to the first irradiation system.

5. The particle therapy system according to claim 1, wherein the second floor includes at least any one of a vertical direction floor configured to apply a particle beam to the second treatment room from a vertical direction and a skew direction floor configured to apply a particle beam to the second treatment room from a skew direction inclined at a predetermined angle from the vertical direction.

6. A particle therapy system comprising:
a building having a first floor and a second floor;
a particle beam generator installed on the first floor, the particle beam generator being configured to generate a particle beam;
a first transport system configured to transport a particle beam from the particle beam generator to a first irradiation system in a first treatment room; and
a second transport system configured to transport a particle beam branched from the first transport system, via the second floor, to a second irradiation system in a second treatment room,
wherein the second transport system has a first bending magnet configured to bend a particle beam to a direction of the second floor, the second floor having a surface that is at a different height from an installation surface of the particle beam generator,
wherein the building has a shielding wall shielding the first floor and the second floor,
wherein the second transport system penetrates the shielding wall on a rear side of the first bending magnet in a traveling direction of a particle beam,
wherein at least a portion of the shielding wall is removed at a predetermined time of expanding the first treatment room by adding the second treatment room,
wherein the second floor includes at least any one of a vertical direction floor configured to apply a particle beam to the second treatment room from a vertical direction and a skew direction floor configured to apply a particle beam to the second treatment room from a skew direction inclined at a predetermined angle from the vertical direction,
wherein the second floor includes the vertical direction floor and the skew direction floor, and
wherein the shielding wall is erected on the vertical direction floor and on the skew direction floor so as to separate the first floor from the vertical direction floor and the skew direction floor.

7. The particle therapy system according to claim 6,
wherein the vertical direction floor is located on an upper side of the skew direction floor, and
wherein the shielding wall is provided in parallel with the skew direction floor as located between the skew direction floor and the first floor so as to separate the first floor from the vertical direction floor and the skew direction floor.

8. The particle therapy system according to claim 7,
wherein, on the vertical direction floor, a vertical direction irradiation system configured to apply a particle beam from the vertical direction is provided as one part of the second irradiation system,
wherein, on the skew direction floor, a skew direction irradiation system configured to apply a particle beam from the skew direction is provided as another part of the second irradiation system;
wherein the first irradiation system applies a first particle beam generated at the particle beam generator, and
wherein the vertical direction irradiation system and the skew direction irradiation system apply a second particle beam generated at the particle beam generator.

9. The particle therapy system according to claim 8, further comprising
a horizontal direction irradiation system configured to apply a particle beam from a horizontal direction.

10. A method of extending a particle therapy system, the method comprising the steps of:
providing a building having a first floor and a second floor;
providing a particle beam generator installed on the first floor, the particle beam generator being configured to generate a particle beam;
providing a first transport system configured to transport a particle beam from the particle beam generator to a first irradiation system in a first treatment room;

providing a second transport system configured to transport a particle beam to a second irradiation system in a second treatment room, the second transport system being branched from the first transport system, via the second floor;
providing, on the second transport system, a first bending magnet configured to bend a particle beam in a direction of the second floor, the second floor having a surface that is at a different height from an installation surface of the particle beam generator;
providing, on the building, a shielding wall configured to shield a space in which the particle beam generator is present on a floor different from the first floor;
disposing the second transport system so as to penetrate the shielding wall on a rear side of the first bending magnet in a traveling direction of a particle beam;
providing, in a midway point of the second transport system, a gate valve on a rear side of the shielding wall on the traveling direction of the particle beam;
blocking the second transport system by the gate valve;
connecting, at a predetermined timing, the second transport system to the second irradiation system in the second treatment room;
opening the gate valve after an inside of the second transport system is maintained at a vacuum; and
removing at least a part of the shielding wall.

* * * * *